US008268365B2

(12) United States Patent
Theoharides

(10) Patent No.: US 8,268,365 B2
(45) Date of Patent: *Sep. 18, 2012

(54) ANTI-INFLAMMATORY COMPOSITIONS FOR TREATING BRAIN INFLAMMATION

(75) Inventor: Theoharis C. Theoharides, Brookline, MA (US)

(73) Assignee: Theta Biomedical Consulting & Development Co., Inc., Brookline, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/861,152

(22) Filed: Aug. 23, 2010

(65) Prior Publication Data

US 2011/0044944 A1  Feb. 24, 2011

Related U.S. Application Data

(63) Continuation of application No. 11/214,831, filed on Aug. 31, 2005, now Pat. No. 7,906,153, which is a continuation-in-part of application No. 10/811,826, filed on Mar. 30, 2004, now abandoned, which is a continuation-in-part of application No. 09/771,669, filed on Jan. 30, 2001, now Pat. No. 6,984,667, which is a continuation-in-part of application No. 09/056,707, filed on Apr. 8, 1998, now Pat. No. 6,689,748.

(51) Int. Cl.
*A61K 36/00* (2006.01)

(52) U.S. Cl. .................................................. 424/725

(58) Field of Classification Search .................. None
See application file for complete search history.

(56) References Cited

U.S. PATENT DOCUMENTS

| | | |
|---|---|---|
| 4,265,823 A | 5/1981 | Nobile |
| 4,447,443 A | 5/1984 | Goldenberg |
| 4,767,778 A | 8/1988 | Arrang et al. |
| 5,223,257 A | 6/1993 | Arora |
| 5,250,529 A | 10/1993 | Theoharides |
| 5,260,335 A | 11/1993 | Wagner et al. |
| 5,434,183 A * | 7/1995 | Larsson-Backstrom ...... 514/549 |
| 5,560,917 A | 10/1996 | Cohen et al. |
| 5,587,363 A | 12/1996 | Henderson |
| 5,648,355 A | 7/1997 | Theoharides |
| 5,661,170 A | 8/1997 | Chodosh |
| 5,747,049 A | 5/1998 | Tominaga |
| 5,795,905 A | 8/1998 | McCarthy et al. |
| 5,804,594 A | 9/1998 | Murad |
| 5,821,259 A | 10/1998 | Theoharides |
| 5,831,259 A | 11/1998 | Charra |
| 5,840,715 A | 11/1998 | Florio |
| 5,855,884 A | 1/1999 | Theoharides |
| 5,858,371 A | 1/1999 | Singh et al. |
| 5,876,744 A | 3/1999 | Della Valle et al. |
| 5,972,999 A | 10/1999 | Murad |
| 5,980,865 A | 11/1999 | Ahmed |
| 5,994,357 A | 11/1999 | Theoharides |
| 6,020,305 A | 2/2000 | Theoharides |
| 6,136,795 A | 10/2000 | Florio |
| 6,162,787 A | 12/2000 | Sorgente et al. |
| 6,211,195 B1 | 4/2001 | Webb et al. |
| 6,271,213 B1 | 8/2001 | Henderson et al. |
| 6,579,544 B1 | 6/2003 | Rosenberg et al. |
| 6,583,123 B2 | 6/2003 | Henderson et al. |
| 6,586,448 B1 | 7/2003 | DeNinno et al. |
| 6,624,148 B2 | 9/2003 | Theoharides |
| 6,635,625 B2 | 10/2003 | Theoharides |
| 6,641,806 B2 | 11/2003 | Theoharides |
| 6,645,482 B2 | 11/2003 | Theoharides |
| 6,689,748 B1 | 2/2004 | Theoharides |
| 6,765,008 B1 | 7/2004 | Chen |
| 6,911,436 B2 | 6/2005 | Brown et al. |
| 6,984,667 B2 | 1/2006 | Theoharides |
| 7,115,278 B2 | 10/2006 | Theoharides |
| 2001/0000340 A1 | 4/2001 | Chen et al. |
| 2002/0009448 A1 | 1/2002 | Weiner et al. |
| 2002/0028779 A1 | 3/2002 | High et al. |
| 2002/0064568 A1 | 5/2002 | Rose et al. |
| 2002/0146393 A1 | 10/2002 | Bell et al. |
| 2004/0005355 A1 | 1/2004 | Theoharides |
| 2004/0039066 A1 | 2/2004 | Crea |
| 2004/0180106 A1 | 9/2004 | Theoharides |

(Continued)

FOREIGN PATENT DOCUMENTS

EP  0426479  5/1991

(Continued)

OTHER PUBLICATIONS

Boushey, R. et al., "Adrenal Cortical Carcinoma," Curr. Treatment Op. Oncol., 2: 355-364 (2001).

(Continued)

*Primary Examiner* — Patricia Leith
(74) *Attorney, Agent, or Firm* — Wilmer Cutler Pickering Hale & Dorr LLP.

(57) ABSTRACT

Compositions with synergistic anti-inflammatory effects in inflammatory diseases resulting from activation and consequent degranulation of mast cells and followed by secretion of inflammatory biochemicals from the activated mast cells, the compositions containing one or more of a flavone or flavonoid glycoside a heavily sulfated, non-bovine proteoglycan, an unrefined olive kernel extract that increases absorption of these compositions in various routes of administration, a hexosamine sulfate such as D-glucosamine sulfate, S-adenosylmethionine, a histamine-1 receptor antagonist, a histamine-3 receptor agonist, an antagonist of the actions of CRR, a long-chain unsaturated fatty acid, a phospholipid, Krill oil, a polyamine, glutiramer acetate and interferon. Certain of the present compositions are useful in protecting against the neuropathological components of multiple sclerosis and similar inflammatory neurological diseases.

19 Claims, No Drawings

U.S. PATENT DOCUMENTS

| | | | |
|---|---|---|---|
| 2005/0220909 A1 | 10/2005 | Theoharides |
| 2005/0220912 A1 | 10/2005 | Theoharides |
| 2006/0013905 A1 | 1/2006 | Tehoharides |
| 2006/0210551 A1 | 9/2006 | Lindsberg et al. |
| 2007/0077317 A1 | 4/2007 | Theoharides |
| 2007/0141187 A1 | 6/2007 | Theoharides |
| 2008/0153761 A1 | 6/2008 | Theoharides |
| 2009/0148543 A1 | 6/2009 | Theoharides |

FOREIGN PATENT DOCUMENTS

| | | |
|---|---|---|
| EP | 1157693 A1 | 11/2001 |
| GB | 2105193 | 9/1984 |
| IT | 1290440 | 9/1998 |
| JP | 2006016531 A | 1/2006 |
| WO | WO-89/05646 | 6/1989 |
| WO | WO-90/06104 | 6/1990 |
| WO | WO-93/09766 | 5/1993 |
| WO | WO-97/21434 | 6/1997 |
| WO | WO-98/33494 | 8/1998 |
| WO | WO-99/21434 | 5/1999 |
| WO | WO-00/78320 | 12/2000 |
| WO | WO-02/060393 A2 | 8/2002 |

OTHER PUBLICATIONS

Cefali, E.A. et al., "Aspirin reduces cutaneous flushing after administration of an optimized extended-release niacin formulations," Int. J. Clin. Pharm. Ther., vol. 45: 78-88 (2007).

Chines, A. et al., "Systemic Mastocytosis Presenting as Osteoporosis: A Clinical and Histomorphometric Study," J. Clin. Endocrinol. and Metab., vol. 72(1): 140-144 (1991).

Database WPI: 2001-358435, "Compositions comprising hyaluronic acid and flavonoids,".

Devlin, Thomas (ed): Textbook of Biochemistry with Clinical Correlations, 2nd Edition: Ch. 8.5-8.6, 345-351 (1982).

Dimitriadou, V. et al., Histochemical and Ultrastructural Characteristics of Rat Brain Perivascular Mast Cells Stimulated With Compound 48/80 and Carbachol, Neuroscience, vol. 39(1): 209-224 (1990).

Dunn, R.T. et al., "Low-Dose Aspirin and Ibuprofen Reduce the Cutaneous Reactions Following Niacin Administration," Am. J. Thera., 2: 478-480 (1995).

Dvorak, A.M. et al., "Human Gut Mucosal Mast Cell: Ultrastructural Observations and Anatomic Variation in Mast Cell-Nerve Associations in vivo," vol. 98: 158-168 (1992).

Gupta, E. et al., "Lovastatin and Extended-Release Niacin Combination Product: The First Drug Combination for the Management of Hyperlipidemia," Heart Disease, vol. 4: 124-137 (2002).

Hendriks, J. et al., "Flavonoids Influence Monocytic GTPase Activity and Are Protective in Experimental Allergic Encephalitis," J. Exp. Med., vol. 200(12): 1667-1672 (Dec. 20, 2004).

International Search Report and Written Opinion, International Patent Application No. PCT/US08/86059, mailed Jan. 26, 2009 (2 pages).

International Search Report issued for PCT/US02/00476, dated Dec. 16, 2002 (6 pages).

International Search Report issued for PCT/US95/01392, dated May 31, 1995 (4 pages).

Irani, A-M, et al., "Mast Cell Changes in Scleroderma," Arth. and Rheuma., vol. 35(8): 933-939 (Aug. 1992).

Kimata, M. et al., "Effects of luteolin, quercetin and baicalein on immunoglobulin E-mediated mediator release from human cultured mast cells," Clin. and Exper. Allergy, vol. 30, 501-508 (2000).

Koblenzer, C.S. "Neurotic excoriations and dermatitis artefacta," Dermatologic Clinics, vol. 14(3): 447-455 (Jul. 1996).

Lambracht-Hall, M. et al., "Serotonin Release From Rat Brain Mast Cells," Neuroscience, vol. 39(1) 199-207 (1990).

Letters to the Editor, J. Allergy Clin. Immunol., vol. 119(2): 498-499 (Oct. 18, 2006).

Lidor, C. et al., "Osteoporosis as the Sole Presentation of Bone Marrow Mastocytosis," J. Bone Min Res., vol. 5(8): 871-876 (1990).

Mathias, J. et al., "Debilitating 'Functional' Bowel Disease Controlled by Leuprolide Acetate, Gonadotropin-Releasing Hormone (GnRH) Analog," Digestive Diseases and Sciences, vol. 34(5): 761-766 (May 1989).

Matsuda, K. et al., "Inhibitory Effects of Sialic-Acid- or N-Acetylglucosamine-Specific Lectins on Histamine Release Induced by Compound 48/80, Bradykinin and a Polyethylenimine in Rat Peritoneal Mast Cells," Jpn. J. Pharmacol., 64: 1-8 (1994).

Mezzapesa, D. et al., "Glatiramer acetate in multiple sclerosis," Expert Rev. Neurotherapeutics (5)4: 451-458 (2005).

Morrow, J. et al., "Indentification of Skin as a Major Site of Prostaglandin D2 Release Following Oral Administration of Niacin in Human," J. Invest. Derm., vol. 98(5): 812-815 (1992).

Morrow, J.D., et al., "Release of markedly increased quantities of prostaglandin D2 in vivo in humans following the administration of nicotinic acid," Prostaglandins, vol. 38(2): 263-274 (1989).

Owens, M.J. and Nemeroff, C.B., "Physiology and Pharmacology of Corticotropin-releasing Factor," Pharmacological Reviews, vol. 43(4): 425-615 (1991).

Parodi et al., "Terfenadine Prophylaxis in Migraine," Arch. Psicol. Neurol. Psichiatr. vol. 49(3): 299-303 (1988).

Pearce, F.L. "Mast cell heterogeneity," TIPS: 165-167 (Apr. 1983).

Read, N. W. "Irritable bowel syndrome (IBS)—definition and pathophysiology,", vol. 130: 7-13 (1987).

Rockoff, S.D. and Armstrong, J.D. "Parathyroid Hormone as a Stimulus to Mast Cell Accumulation in Bone," Calc. Tiss. Res., 5: 49-55 (1970).

Russell, A.L. and McCarty, M.F. "Glucosamine for migraine prophylaxis?" Medical Hypotheses, 55(3): 195-198 (2000).

Seibold, J. et al., "Dermal Mast Cell Degranulation in Systemic Sclerosis," Arth. and Rheuma., vol. 33(11): 1702-1709 (Nov. 1990).

Shapiro, G. et al., "Cromolyn Sodium: A Review," Pharmacotherapy, vol. 5(3): 156-170 (May/Jun. 1985).

Shoskes, D., et al., "Quercetin in men with category III chronic prostatis: a preliminary prospective, double-blind, placebo-controlled trial," Urology, 54(6): 960-963 (1999).

Simopoulos, A.P., Visioli F. (eds): Mediterranean Diets. World Rev. Nutr. Diet. Basel, Karger, vol. 87: 56-77 (2000).

Split et al., "Ketotifen in the treatment of Chronic ClusterHeadache," Headache, vol. 24(30: 147-148: 1984).

Stefanini, G.F. et al., "Oral disodium cromoglycate treatment on irritable bowel syndrome: An open study on 101 subjects with diarrheic type," vol. 87: 55-57 (1992).

Sundaram, K. et al., "Antagonists of luteinizing hormone releasing hormone bind to rat mast cells and induce histamine release," Agents and Actions, vol. 25(3/4): 307-313 (1988).

Tauberg, J. et al., "Stress-induced urticaria associated with local anesthetic administration," Anesthesia Progress, vol. 30(6): 199-200 (1983).

Theoharides, T. "Mast Cells and Migraines," Brief Proposal, (1983).

Theoharides, T. et al., "Bladder Mast Cell Activation in Interstitial Cystitis," Seminars of Urology, vol. IX(2): 74-87 (May 1991).

Theoharides, T.C. "Mast Cells: The Immune Gate to the Brain," Life Sciences, vol. 46: 607-617 (1990).

Theoharides, T.C. and Douglas, W.W. "Somatostatin Induces Histamine Secretion From Rat Peritoneal Mast Cells," Endocrinology, vol. 102(5): 1637-1640) (Nov. 7, 1977).

Theoharides, T.C., "Histamine2 (H2)-Receptor Antagonists in the Treatment of Urticaria," Drugs 37: 345-355 (1989).

Theoharides, T.C., "The Mast Cell: A Neuroimmunoendocrine Master Player," Int. J. Tiss. Reac. XVIII(1), 1-21 (1996).

Trichopoulou, A. et al., "Cancer and Meditarranean Dietary Traditions," Cancer Epidemiology, Biomarkers, & Prevention, vol. 9: 869-873 (Sep. 2000).

Trichopoulou, A. et al., "Diet and Survival of Elderly Greeks: a link to the pastl-4." Am. J. Clin. Nutri., vol. 61(suppl.): 1346S-50S (1995).

Tsakalos, N, et al., "Induction of Mast Cell Secretion by Parathormone," vol. 32(2): 355-360 (1983).

Unlisted Drugs, vol. 20(11): 167 (Nov. 1968).

Urade, Y. et al., "The Major Source of Endogenous Prostaglandin D2 Production is Likely Antigen-Presenting Cells," J. Immunol., 143(9): 2982-2989 (Nov. 1, 1989).

Verbeek, R. et al., "Oral flavonoids delay recoverly from experimental autoimmune encephalomyelitis in SJL mice," Biochem. Pharm., 70: 220-228 (2005).

Weston, A. et al., "Terminal Ileal Mucosal Mast Cells in Irritable Bowel Syndrome," Dig. Diseases and Sci., vol. 38(9): 1590-1595 (Sep. 1993).

Webster et al., "In Vivo and In Vitro Characterization of Antalarmin, A Nonpeptide Corticotropin-Releasing Hormone (CRH) Receptor Antagonist: Suppression of Pituitary ACTH Release and Peripheral Inflammation," Endocrinology 137(12): 5747-5750 (1996).

Arrang et al. "Preparation of a, B-Dimethylhistamine and stereoisomers as selective . . . " Chemical Abstracts, 113(3):23542U, Jul. 16, 1990.

Oishi et al. "Effects of the Histamine H3-Antagonist®-a Methylhistamine and the antagonist . . . " J Neurochemistry 52(5):1388-1392, 1989.

Mansfield, "The role of Antihistamine Therapy in Vascular Headaches," J Allergy Clin. Immunol., 86(4 Pt. 2):673-6, Oct. 1990 (Abstract).

Strassman et al. "Sensitization of meningeal sensory neurons and the origin of headaches" Nature, vol. 384, Dec. 1996, 560-564.

Martinez-Dominguez et al. "Protective effects upon experimental inflammation models of a polyphenol-supplemented virgin olive oil diet" Inflamm. Res. 50:102-106 (2001).

Shute "Aching for an arthritis cure" US News and World Report, Feb. 1997 (2 pages).

Cowley "The arthritis cure?" Newsweek, Feb. 1997 (2 pages).

Foreman "People, their pets, and arthritis" The Boston Globe, Apr. 1997 (4 pages).

Tye, L. "Boom for Joint Drug Prods Scientific Study," The Boston Globe, Sep. 2000 (3 pages).

McAlindon et al "Glucosomaine and Chondroitin for Treatment of Osteoarthritis" J Am Med Assn 283:11, 1469-1475 (2000).

Reginster at al. "Long-term effects of glucosamine sulphate on osteoarthritis progression: a randomised, placebo-controlled clinical trial" Lancet vol. 357:251-256 (2001).

Theoharides, T.C., "Chondroitin sulphate inhibits connective tissue mast cells," British Journal of Pharmacology 131:1039-1049 (2000).

Galli "New Concepts about the Mast Cell" N. Eng J Med. 328:257-265 (1993).

Theoharides, "Interstitial Cystitis: A Neuroimmunoendocrine Disorder" New York Academy of Sciences 840:619-634 (1998).

Theoharides, TC., "The role of mast cells in migraine pathophysiology," Brain Res Rev. 49:65-76 (2005).

Theoharides, T. "Mast Cells: The Immune Gate to the Brain," Life Sci 46:607-617 (1996).

Middleton et al. "The Effects of Plant Flavonoids in Mammalian Cells: Implications for Inflammation, Heart Disease, and Cancer" Pharm Rev 52:673-751 (2000).

Theoharides et al. "Cloning and Cellular Localization of the Rat Mast Cell 78-kDa Protein Phosphorylated in Response to the Mast Cell 'Stabilizer' Cromolyn" J Pharm Exp Therap 294:3; 810-821 (2000).

Kempuraj et al. "Flavonols inhibit proinflammatory mediator release, intracellular calcium ion levels and protein kinase C theta phosphorylation in human mast cells" Br. J. Pharmacol. 2005: 1-11.

Odontuya G. et al. "Structure-Activity Relationship for Antiinflammatory Effect of Luteolin and its Derived Glycosides" Phytother. Res. 19:782-786 (2005).

Del Carlo et al. "Contribution of the Phenolic Fraction to the Antioxidant Activity and Oxidative Stability of Olive Oil" J Agr Food Chem 52:4072-4079(2004).

Bacon et al. "Nails in the Coffin: Increasing Evidence for the Role of Rheumatic Disease in the Cardiovascular Mortality of Rheumatoid Arthritis," Arthritis & Rheumatism, vol. 44(12) 2707-2710 (2001).

Schwartz M. et al. "Protective autoimmunity and neuroprotection in inflammatory and noninflammatory neurodegenerative diseases". J. Neurol. Sci. 233:163-166 (2005).

Arnon et al. "Mechanism of action of glatiramer acetate in multiple sclerosis and its potential for the development of new applications" Proc. Nat. Acad. Sci. USA vol. 101, Suppl. 2:14593-14598 (2004).

Kandere-Grzybowska, K. "IL-1 Induces Vesicular Secretion of IL-6 without Degranulation from Human Mast Cells," et al. J Immun. 171:4830-4836 (2003).

Ip, M. et al. "Functionality of estrogen receptor and tamoxifen treatment of R3327 dunning rat prostate adenocarcinoma," Cancer Research, vol. 40, p. 2188-2193 (1980).

Widyarini et al. "Isoflavanoid compounds from Red Clover (*Trifolium pretense*) Protect from Inflammation and Immune Suppression Induced by UV Radiation" Photochemistry and Photobiology, 2001, vol. 74, No. 3, pp. 465-470.

Spanos "Stress-induced Bladder Mast Cell Activation: Implications for Interstitial Cystitis". J Urol 157:669-672, 1997.

Pang "Mast Cell and Substance P-Positive Nerve Involvement in A Patient With Both Irritable Bowel Syndrome and Interstitial Cystitis" Urology 47:3, 436-438 (1996).

Castagliuolo et al. "Acute stress causes mucin release from rat colon: role of corticotropin releasing factor and mast cells" Am J Physiol 274: 884-892 (1996).

Theoharides, "Corticotropin-Releasing Hormone Induces Skin Mast Cell Degranulation and Increased Vascular Premeability, A Possible Explanation for Its Proinflammatory Effects" Endocrinology 139:1; 403-413 1998.

Longley at al "The mast cell and mast cell disease" J Am Acad Dermatol 32:4; 545-561, 1995.

Devlin "Textbook of Biochemistry" pp. 347-351, 1986.

Middleton et al, "Effects of Flavonoids on Immune and Inflammatory Cell Functions" Biochem Pharm 43:6 1167-1179 (1992).

Theoharides, "The Pharmacologist". 39(4), Abs. 9700, Dec. 10, 1997, Meeting Apr. 18-Apr. 22, 1998.

Bauman, N. "Mast cells may account for success of GAG layer treatments.", Urology Times, 26, (3 pages) Mar. 1998.

Parsons, C.L. et al. "Treatment of interstitial cystitis with intravesical heparin," Brit J. Urol. 73:504-507 (1994).

Porru et al. "Results of Treatment of Refractory Interstitial Cystitis with Intravesical Hyaluronic Acid," Urol Int. 59:26-29 (1997).

Bosku, "Olive Oil" Mediterranean Diet—World Rev. Nutr. Diet, 87:56-77 (2000).

Libby "The Forgotten Majority; Unfinished business in cardiovascular risk reduction" J Am College Cardiol. vol. 46:7; 1225-1228 (2005).

Carlson "Nicotinic acid: the broad-spectrum lipid drug. A 50th anniversary review"J Intern. Med. 258:94-114 (2005).

Brown BG et al. "Simvastatin and Niacin, Antioxidant Vitamins, or the Combination for the Prevention of Coronary Disease" N. Eng J Med. 345:22, 1583-1592 (2001).

Meyers et al. "Nicotinic acid induces secretion of prostaglandin D2 in human macrophases; An in vitro model of the niacin flush" Atherosclerosis 192 (2007) 253-258.

Urade et al. "Localization of Glutathione-Requiring Prosaglandin D Synthetase in Histiocytes, Dendritic, and Kupffer Cells in Various Rat Tissues" J Immunol. vol, 142, pp. 2982-2989, No. 9 (1989).

Grutzkau et al. "Synthesis, Storage, and Release of Vascular Endothelial Growth FactorNascular Permeability Factor (BEGF/VPF) by Human Mast Cells" Mol. Cell. Biol. 9:875-884 (1998).

Boesiger et al. "Mast Cells Can Secrete Vascular Permeability Factor/Vascular Endothelial Cell Growth Factor and Exhibit Enhanced Release after Immunoglobulin E-dependent Upregulation of FcE Receptor I Expression "J Exp. Med 188:6, 1135-1145 (1998).

Kushnir-Sukhov, "Human mast cells are capable of serotonin synthesis and release," Letters to the Editor, J Allerg. Clin Immunol. vol. 119, No. 2, pp. 498-499 (2006).

Grant, "Food; Fish without the fuss" Sunday Mirror, London, Sep. 3, 2000, (5 pages).

Ronca "Anti-Inflammatory Activity of Chondroitin Sulfate" Osteoarthritis and Cartilage (1998) pp. 14-21.

Starbuck, J. "Elderberry 7 Cat's Claw Wisely Harnessing the Power of Herbs for Immune-Boosting and More" Better Nutrition, Atlanta Sep. 1998, vol. 60, Issue 9, pp. 54 (4 pgs).

Chandrasekar "Tissue Specific Regulation of Transforming Growth Factor Beta by Omega-3 Lipid-Rich Krill Oil in Autoimmunite Murine Lupus" Nutritional Research, vol. 16, No. 3 (489-503) (1996).

Olive Seed Oil: OSUMEX <www.osumex/olive.php> accessed Jun. 27, 2006 pp. 1-2.

Quercetin: The Mens Health Shop <www.ishop.co.uk/ishop/451/shopscr130.html> accessed Jun. 27, 2006, 1 pg.

Scott et al. "Nonsteroidal Antiinflammatory Agents in the Management of Canine Pruritis" Journal of American Animal Hosp. Assoc. Jul./Aug. 1988 vol. 24, pp. 425-428.

www.orthop.washington.edu/uw/tabID_3411/default.aspx, printed Jul. 9, 2010 (3 pages).

Danielov, Chemical Abstracts, vol. 125, #132809 (2 pages), Sep. 9, 1996.

Dr. Duke, "Phytochemical and Ethnonobotanical Database" <www.ars-grin.gov/cgi-bin/duke/farmacy2.pl> p. 1-5, printed Feb. 19, 2010.

* cited by examiner

ANTI-INFLAMMATORY COMPOSITIONS FOR TREATING BRAIN INFLAMMATION

This application is a continuation of U.S. application Ser. No. 11/214,831, filed Aug. 31, 2005, which is a continuation-in-part application of U.S. patent application Ser. No. 10/811,826, filed Mar. 30, 2004, which is a continuation-in-part application of U.S. patent application Ser. No. 09/771,669, filed Jan. 30, 2001, now U.S. Pat. No. 6,984,667, which is a continuation-in-part application of U.S. patent application Ser. No. 09/056,707, filed Apr. 8, 1998, now U.S. Pat. No. 6,689,748.

BACKGROUND OF THE INVENTION

The invention is generally related to the treatment of inflammatory conditions. More specifically, the invention is related to compositions containing inhibitors of mast cell activation and secretion such as a proteoglycan and a flavonoid compound that are designed to be used as dietary supplements or adjuvants to conventional approved medications for the relief of inflammatory conditions, e.g., in the brain as in multiple sclerosis.

There have been a number of mostly anecdotal reports that the proteoglycan chondroitin sulfate, as well as glucosamine sulfate, a product of the intestinal breakdown of proteoglycans, may be helpful in relieving the pain of osteoarthritis:— Shute N. Aching for an arthritis cure. *US News and World Report*, Feb. 10, 1997.—Cowley, G. The arthritis cure? *Newsweek*, Feb. 17, 1997; Foreman J., People, and their pets, tout arthritis remedy. *The Boston Globe*, Apr. 7, 1997; Tye L. Treatment gains scientific attention. *The Boston Globe*, Sep. 25, 2000.

A meta-analysis showed potential therapeutic benefit of chondroitin sulfate and/or glucosamine in osteoarthritis [McAlindon, et al. *J. Am. Med. Assn.* 283:1469 (2000)], while a double-blind clinical trial with glucosamine showed definite benefits in osteoarthritis with respect to both pain and radiographic joint appearance [Reginster, et al., *Lancet* 337: 252 (2001)]. However, less than 5% of the chondroitin sulfate in commercially available preparations is absorbed orally, because the size of the molecule and the degree of sulfation impede its absorption from the gastrointestinal tract. Furthermore, such commercial preparations use chondroitin sulfate obtained from cow trachea, with the possible danger of contracting spongioform encephalopathy or "mad cow disease". In fact, the European Union has banned even cosmetics that contain bovine-derived products.

Theoharides, et al., *British Journal of Pharmacology* 131: 1039 (2000) indicated for the first time how proteoglycans, such as chondroitin sulfate, may work. This paper reported that chondroitin sulfate and, to a lesser degree, glucosamine sulfate, inhibit activation of mast cells that are known to trigger allergy and asthma. This discovery is the basis for Theoharides, T. C., U.S. Pat. No. 6,689,748 and Ser. No. 09/773,576, filed Feb. 2, 2001.

Mast cells are also now recognized as important causative intermediaries in many painful inflammatory conditions [Galli, *N. Eng. J. Med.* 328:257 (1993); Theoharides, *Int. J. Tissue Reactions* 18:1 (1996)], such as interstitial cystitis and irritable bowel syndrome [Theoharides, T. C., *Ann. NY Acad. Sci.* 840:619 (1998)], as well as in migraines [Theoharides, T. C., *Brain Res. Rev.* 49:65 (2005) and possibly multiple sclerosis [Theoharides, T. C., *Persp Biol Med.* 26:672 (1983), Theoharides, *Life Sci.* 46:607 (1996), and *J. Neuroimmunol.* 146:1 (2004).

Mast cells are increasingly implicated in conditions involving inflamed joints, such as in osteoarthritis and rheumatoid arthritis, through activation of local mast cells by, for example, neuropeptides, such as Substance P. Additional indirect evidence also supports the involvement of mast cells in bone resorption: (a) systemic mastocytosis is invariably associated with osteoporosis; (b) inhibition of mast cell mediator release reversed lytic bone changes; (c) depletion of mast cells inhibited bone resorption in organ culture; (d) human synovial mast cells were shown to secrete in response to allergic and non-immunologic stimuli; (e) human mast cells release the cytokine IL-6; and (f) IL-6 has been definitively linked to bone resorption and osteoporosis.

It was shown that chondroitin sulfate's ability to inhibit the activation of mast cells compliments the inhibitory effects on mast cell activation of another class of naturally occurring compounds, the flavonoids [Middleton, et al., *Pharm. Rev.* 52:1 (2000)]. Certain plant flavones (in citrus fruit pulp, seeds, sea weed) are now recognized as anti-allergic, anti-inflammatory, anti-oxidant and cytoprotective with possible anti-cancer properties. Only some flavonoids, especially those belonging to the subclass of flavonols, e.g., quercetin, inhibit mast cell activation.

Quercetin inhibits secretion from human activated mast cells [Kimata, et al., *Allergy* 30:501 (2000)], and has also been used effectively for the treatment of chronic prostatitis [Shoskes, et al., *Urology* 54:960 (1999)]. However, other flavonoids may have opposite effects. Use of the term "bioflavonoids" or "citrus flavonoids" in certain commercial products, therefore, provides little information, and may include molecules that have detrimental effects; for example, soy contains isoflavones that have estrogen-like activity that worsens inflammatory conditions.

U.S. Pat. No. 6,689,748, and divisional application Ser. No. 09/773,576 claim the oral use of proteoglycans, without and with flavonoids, for the treatment of mast cell activation-induced diseases. Absorption of these compositions from the gastrointestinal tract and synergism with other treatment modalities were not addressed in these applications.

Applicant has described the use of antagonists of the action of Corticotropin Releasing Hormone ("CRH") (also known as Corticotropin Releasing Factor) in inhibiting myocardial mast cell activation in myocardial ischemia, in treating stress-induced skin disease (U.S. Pat. No. 6,020,305) and stress-induced migraine headaches (U.S. Pat. No. 5,855,884), the contents of which are incorporated herein by reference. The synergistic effects of the compositions of the present invention that include antagonists of the actions of CRH on mast cells were not recognized at the time of the previous studies. The word "antagonists" in connection with CRH is intended herein to include any molecule that prevents the actions of CRH on target cells, and includes, but is not limited to, anti-CRH neutralizing antibodies or binding proteins, or molecules preventing the release of CRH at local sites (see below for details).

Applicant has also described a method for treating patients with mast cell derived molecules-induced interstitial cystitis with certain histamine-I receptor antagonists (Theoharides, U.S. Pat. No. 5,994,357). Treatment of mast cell molecules-induced migraines with histamine-3 receptor agonists is the subject of Theoharides U.S. Pat. No. 5,855,884. Histamine-3 receptor agonists as pharmaceutical agents in mast cell-involved diseases are described in Theoharides, U.S. Pat. No. 5,831,259. The contents of these three patents are incorporated herein by reference. At the time of this invention the synergistic effects of the present compositions with such antagonists had not yet been recognized.

An important need therefore exists for compositions for administration to human patients being treated for mast cell-induced inflammatory diseases by various modalities, that are synergistic in that they have stronger effects than the sum of the effects of the individual components, and also synergistic with conventional clinical treatments of inflammatory conditions. "Synergistic" is also intended to mean: "coordinated or correlated action by two or more structures or drugs"[*Stedman's Medical Dictionary*, 23$^{rd}$ ed., Williams & Wilkins, Baltimore, 1976]. An important need also exists for formulations that increase the absorption from the gastrointestinal tract, nasal passages and skin surface of the compositions of the invention. Such formulations have been discovered, and are described below.

SUMMARY OF THE INVENTION

The invention comprises compositions for human use containing one or more of a flavonoid compound, a non-bovine heavily sulfated proteoglycan, an unrefined olive kernel extract, a sulfated hexosamine, S-adenosylmethionine ("SAM"), histamine-1 receptor antagonists, histamine-3 receptor agonists, antagonists of the actions of CRH, folic acid, a straight chain polyunsaturated fatty acid, a phospholipid, a polyamine, an interferon and glutiramer acetate, together with appropriate excipients and carriers, said compositions having improved absorption from the gastrointestinal tract, skin surface, and nasal and pulmonary surfaces, and anti-inflammatory effects synergistic with each other and synergistic with available conventional clinical treatment modalities.

In one embodiment, the sulfated glucosamine is D-glucosamine sulfate, the proteoglycan is non-bovine chondroitin sulfate, and the flavonoid is quercetin (3,3',4',5,7-pentahydroxy flavone), the quercetin glycoside rutin, myricetin, genistein, kaempferol, luteolin, apigenin, (−)-epigallocatechin-3 gallate, kaempferol or the kaempferol glycoside astragaline, or hesperitin or its glycoside hesperidin.

In another embodiment, compositions may also contain antagonists of the effects of CRH on mast cells or other target cells of the myocardium, gastric mucosa, urinary bladder, skin, meningeal membranes, blood-brain barrier, and brain structures.

In still another embodiment, the inventive compositions are used against superficial vasodilator flush syndromes.

In still another embodiment, the inventive compositions may be used as coatings on medical devices, not only to protect surrounding tissues from inflammation due to the devices, but also to treat innate inflammation in surrounding tissues.

In another embodiment, the inventive compositions are used against the inflammatory processes of endometriosis.

In yet another embodiment, the inventive compositions are used against the inflammatory components of hormonally-related cancers, such as breast, ovarian, uterine, prostate and testicular cancers, and when supplemented with chemotherapeutic agents are used against the cancer itself.

In still another embodiment, the inventive compositions may be used in the treatment of the neuroinflammatory aspects of multiple sclerosis.

In another embodiment, the inventive olive kernel extract is used to improve the absorption of biochemicals across membrane barriers in the body, such as those of the intestine, skin, oral mucosa, blood-brain barrier, and pulmonary alveoli.

In yet another embodiment, the inventive compositions may be used in the treatment of fibromyalgia or chronic fatigue syndrome.

DETAILED DESCRIPTION OF THE PREFERRED EMBODIMENTS OF THE INVENTION

It has been discovered that various combinations of a sulfated proteoglycan, unrefined olive kernel extract, a flavone (a.k.a. flavonoid compound), a sulfated D-hexoseamine, a phospholipid, a long chain unsaturated fatty acid, a CRH antagonist, a histamine-1 receptor antagonist, a histamine-3 receptor agonist, glutiramer acetate, an interferon, and a polyamine have synergistic anti-inflammatory effects when used as a dietary supplement, a topical product or an aerosol for nasal or pulmonary administration, without or with a conventional clinical treatment for inflammatory diseases. Within the present context, such inflammatory diseases result from the activation, degranulation and consequent secretion of inflammatory biochemicals from mast cells, and the resultant inflammatory diseases include the group consisting of: allergic inflammation, arthritis (to include osteoarthritis and rheumatoid arthritis), fibromyalgia, chronic fatigue syndrome, inflammatory bowel disease, interstitial cystitis, irritable bowel syndrome, migraines, atherosclerosis, coronary inflammation, ischemia, chronic prostatitis, eczema, multiple sclerosis, psoriasis, sun burn, periodontal disease of the gums, superficial vasodilator flush syndromes, hormonally-dependent cancers, and endometriosis. The olive kernel extract alone may be used to improve the transmembrane transport of difficulty-absorbable biomolecules in the intestine, skin and pulmonary alveoli.

In a highly preferred embodiment, the sulfated proteoglycan is non-bovine chondroitin sulfate, preferably from shark cartilage, which blocks mast cell activation, degranulation and consequent secretion of inflammatory biochemicals from the mast cells. Other natural sulfated proteoglycans suitable for practicing this invention include keratan sulfate, dermatan sulfate and hyaluronic acid sodium salt (sodium hyaluronate). The preferred biological source of the chondroitin sulfate is shark cartilage which is more-highly sulfated than the common commercial chondroitin sulfate isolated from cow trachea; the shark cartilage source also avoids the potential dangers associated with bovine sources.

A highly preferred flavonoid is quercetin which inhibits secretion of inflammatory molecules from mast cells by affecting moesin, a unique 78 kDa mast cell protein [Theoharides, T C, et al., *J Pharm. Exp. Therap.* 294:810 (2000), Kempuraj, et al., *Br. J. Pharmacol.* 145:934 (2005)]. In addition to quercetin, other flavonoids suitable in carrying out the invention include: the quercetin glycoside rutin, myricetin, genistein, luteolin, apigenin, (−)-epigallocatechin-3 gallate, kaempferol and the kaempferol glycoside astragaline, hesperitin and its glycoside hesperidin.

The olive kernel extract product component of the inventive compositions is preferably an unrefined (first pressing, filtered, oleic acid-related acidity <3%, water content <1%) extract product produced, for one source, on the island of Crete in Greece. This kernel extract product is especially prepared by applicant's process consisting essentially of:
(1) harvesting first collection ripe olives, preferably in December; (2) compressing the oil from the flesh of the ripe olives; (3) washing the kernels remaining after step (2) with water to remove debris; (4) drying the washed kernels with a stream of hot air; (5) crushing the dried kernels to produce an extract; (6) extracting the extract from step (5) with an organic solvent (e.g., hexane, heptane, octane) plus steam; (7) removing particulate matter from the organic extract by centrifugation or microfiltering through 1-2 micron pore size filters; (8) evaporating the organic solvent and water from the clarified extract of step (7) by maintaining the extract at 86-100 degrees C. while percolating helium (to avoid oxidation) through the fluid, which process reduces the water content to <1%, the acidity (as oleic acid) to <3%; and, the organic solvent to <1%; and (8) storing the final kernel extract product in the absence of air.

The inventive olive kernel extract surprisingly has the unique property of increasing absorption of the other components of the anti-inflammatory compositions through the intestinal mucosa or skin, and also adds its own content of important anti-oxidants, such as omega fatty acids (e.g., eicosapentanoic acid) and alpha tocopherol. The polyphenols found in such olive kernel extracts also have anti-inflammatory effects in, for example, arthritis [Martinez-Dominguez, et al., *Inflamm. Res.* 50:102 (2001)]. E.B.E.K., Inc., Commercial, Industrial Enterprises of Crete, 118 Ethnikis Antistasecos, Heraklion, Crete, 71306, Greece, or MINERVA SA. Edible Oil Enterprises, 31 Valaoriton S1., Metamorphosis, Attizes, Greece will prepare the extract product according to applicant's above-described procedure for commercial users.

In addition to its usefulness in increasing the absorption of the inventive macromolecular compositions across the intestinal wall and the skin, the inventive olive kernel extract product is useful in aiding the dissolution of other drugs prior to administration to a patient, and is useful in promoting the absorption of other difficultly-absorbable drugs, e.g., the HDL-increasing drug torcetrapib across intestinal mucosa, oral mucosa, nasal mucosa, and skin of patients.

Supplementation of the compositions described above with the methylation reagent S-adenosylmethionine ("SAM") adds antioxidant, anti-inflammatory and cytoprotective properties, particularly in inflammatory joint and cardiovascular diseases. Addition of SAM also accelerates metabolism of homocysteine, which amino acid has been implicated in coronary disease, to cysteine, which is harmless. Folic acid may be added to certain of the present formulations for similar reasons.

Another supplement to the basic compositions of the invention is a histamine-1 receptor antagonist, such as hydroxyzine, merelastine, azelastine, azatadine, rupatadine, and cyproheptadine. Other histamine-1 receptor antagonists are described in Table 25-1 in Goodman and Gilman's *The Pharmaceutical Basis of Therapeutics*, 9th ed., New York, 1996. Histamine-3 receptor agonists are described in the Theoharides patents listed above.

Inhibitors of mast cell activation and secretion of inflammatory biochemicals may be used in the treatment of inflammatory processes such as superficial vasodilator syndrome, such as occurs in menopausal-associated flush, carcinoid flush, MSG-associated flush, and niacin-associated flush.

Hormone-dependent cancers, including the estrogen/progestin linked ovarian, uterine, breast, and endometrial cancers, and the androgen-linked prostate and testicular cancers, are associated with tissue inflammation. These conditions can be treated with chondroitin sulfate, quercetin, genistein, rutin, phenoxodiol isoflavone, (–)-epigallocatechin-3-gallate, olive kernel extract, and, optionally, chemotherapeutic agents such as tomoxifen or raloxifen.

Pelvic inflammatory conditions, such as present in endometriosis, can also be treated with the inventive compositions. Particularly useful in this regard are compositions delivering 50-300 mg/day of rutin, quercetin, kaempferol, myricetin, or hesperitin.

The inventive compositions may also be used as coatings on implanted medical devices, which devices may lead to or be associated with inflammation of surrounding tissues, in order to provide protection against such inflammations. Not only can the coating of such medical devices inhibit or protect against inflammation caused by the device itself, but the coated devices can also be used to deliver the inventive compositions to innately inflamed tissues due to other causes. Such medical devices include artificial skins (scaffolding such as naturally occurring polymers, e.g., collagen; man-made polymers, e.g., PTFE, Dacron, PET or polyethylene; self-degrading man-made polymers, e.g., PLA or PGA; biopolymer matrices from animal tissues including fetal and neonatal tissues to be used as tissue engineering scaffolds (cf. Bell et al., U.S. patent application Pub. No. 20020146393)), artificial joints, band-aids, stents for blood vessels, artificial blood vessels, pacemakers, stents for abdominal support in hernia repair, tissue transplants, prostheses, breast implants, etc. Particularly useful in this regard are compositions containing heavily sulfated, non-bovine proteoglycans (e.g., chondroitin sulfate) and a flavonoid.

Oral flavonoids, such as those listed above, are reported to influence the course of experimental autoimmune encephalomyelitis in mice, a model for multiple sclerosis [Verbeck, R., et al., *Biochem. Pharm.* 70(2):220 (Jul. 15, 2005); Hendriks, J. J., et al., *J Exp Med.* 200(12):1667 (Dec. 20, 2004). In preferred embodiments of the inventive compositions, flavonoids or flavonoid glycosides plus one or more of a proteoglycan, olive kernel extract, Krill oil, hydroxyzine, (–)epigallocatechin-3-gallate, and a long chain fatty acid plus injections of interferon and/or glutiramer acetate (Copolymer I) (Copaxone, TEVA Pharmaceuticals, Israel; Avonex, Biogen., USA) are used in treatment of the chronic inflammation of the central nervous system in multiple sclerosis. The glutiramer acetate is of particular value in preventing relapsing/remitting forms of multiple sclerosis [Mezzapesa, D. M., et al., *Exper. Rev. Neurother.* 5:451 (2005); Schwartz, M., et al., *J. Neurol. Sci.* 233:163 (2005); Amon, R., et al., *Proc. Nat. Acad. Sci. USA* 102 Suppl. 2:14593 (2004)].

Sources of CRH antagonists include, in addition to the Theoharides patents listed in the Background section above: Neurocrine Biochem. Inc.'s D-Phe 12 Nle Ala32,21, 38hCRH(12-41)NR2, cat no. 1P-36-41; Pfizer non-peptide CP-154, 526-1; Sigma Chem., St. Louis anti-CRH polyclonal antiserum; and Pfizer, NY patents and applications: U.S. Pat. No. 6,211,195, U.S. Pat. No. 5,795,905, PCT/IB95/00573, PCT/IB95/00439, U.S. Ser. No. 08/448,539, U.S. Ser. No. 08/481,413, U.S. Ser. No. 09/735,841, and in Owens et al. *Pharm. Rev.* 43:425 (1991).

The preferred concentration range of the proteoglycan, hexosamine sulfate, flavonoid, polyunsaturated fatty acid, phospholipid components of the oral formulations are 10-3,000 mg per tablet or capsule. The preferred concentration range for SAM is 3-1,000 mg per capsule or tablet. Generally, where present, the amounts of the unrefined olive kernel extract are at least twice those of the other active ingredients, preferably 300-1200 mg. The number of capsules or tablets to be taken per day is determined by the nature and severity of the medical condition, and is readily determinable by the patient's health provider. Other representative formulations are described in the examples below.

The compositions of the invention may be formulated in any standard means of introducing pharmaceuticals into a patient, e.g., by means of tablets or capsules. The compositions of the invention include ointments and creams for skin conditions, mouth washes and toothpaste for periodontal diseases, and solutions for nasal aerosols. Standard excipients and carriers for the active ingredients of the inventive compositions are described in *Remington's Pharmaceutical Sciences*, Mack Publishing Co., Easton, Pa.

Although not bound by any particular mechanism of action of the components of the claimed compositions, the inventor contemplates that they inhibit the activation and degranulation of the relevant mast cells, and inhibit the secretion of inflammatory biomolecules from these mast cells. "Activation" and "degranulation" of mast cells are defined herein as is standard and well known in this art, that is, to mean synthesis and secretion from the activated mast cell of any type of molecule(s) that alone or in combination triggers inflammation.

EXAMPLES

Example 1

Table 1 compares chondroitin sulfate-containing commercial products to the present compositions.

In all examples, chondroitin sulfate is assumed to be of a non-bovine variety.

Example 2

Composition For Protecting Against Inflammatory Diseases
Two capsules to be taken orally 2-3 times daily, at least one hour before meals

| Ingredients, per capsule, | mg: |
| --- | --- |
| Chondroitin sulfate | 150-300 |
| D-Glucosamine sulfate | 150-300 |
| Quercetin | 150-300 |
| Olive kernel extract | 350-1200 |

TABLE 1

Comparison of Chondroitin Sulfate-Containing Products to Present Invention

| Product | Most Available Compositions | Present Invention |
| --- | --- | --- |
| Main ingredient | Mixture of chondroitins | Non-bovine chondroitin sulfate, preferably the C type |
| Source | Cow trachea | Shark cartilage |
| Amount per capsule or tablet | 100-300 | 10-3000 mg |
| Degree of sulfation | Low, if any | High |
| Absorption from g.i. tract | <5% | >15% |
| Target | Unknown | Mast cells, inflammatory cells |
| Other ingredients | Vitamins, fish oils (some preparations) | Flavones, unrefined olive kernel extract, SAM, histamine-1 receptor antagonists, histamine-3 receptor agonists, CRH antagonists, polyamines, caffeine, folic acid |
| Advantages | None known | Anti-allergic, anti-inflammatory, antioxidant, cytoprotective |
| Adverse Effects | Risk of mad cow disease, spongiform encephalopathy, stomach upset, allergy to fish products | None known |
| Relevant conditions | Osteoarthritis | Allergic inflammation angina, asthma coronary artery disease, arthritis (osteoarthritis or rheumatoid arthritis), chronic prostatitis, eczema, fibromyalgia, interstitial cystitis, irritable bowel syndrome, inflammatory bowel disease, migraines, multiple sclerosis, psoriasis, periodontal disease, flush syndrome, cancer (including hormonally-dependent forms). |
| Scientific publications | None found | Theoharides, et al. Br. J. Pharm. 131: 1039 (2000) Middleton, et al. Pharm. Rev. 52: 673 (2000) |

Example 3

| Composition For Protecting Against Arthritis | |
|---|---|
| Ingredients, per capsule, | mg: |
| D-Glucosamine sulfate | 150-300 |
| Chondroitin sulfate | 150-300 |
| Sodium hyaluronate | 100-200 |
| Quercetin | 150-300 |
| Olive kernel extract | 350-1200 |

Example 4

| Topical Composition For Protecting Against Arthritis Skin ointment or cream. Apply three times per day to affected areas. | |
|---|---|
| Ingredients | % by weight |
| D-glucosamine sulfate | 5 |
| Chondroitin sulfate | 5 |
| Sodium hyaluronate | 0.5 |
| Bitter willow bark extract | 5 |
| Quercetin | 3 |
| Aloe vera | 10 |
| Olive kernel extract | 5 |

Example 5

| Composition For Protecting Against Cardiovascular Inflammatory Disease | |
|---|---|
| | mg/capsule: |
| *Chondroitin sulfate | 50 |
| *Kaempferol | 100 |
| *S-adenosylmethionine | 50 |
| *Niacin | 0.01 |
| *Olive kernel extract | 350-1200 |
| *Bitter willow bark extract | 5% by weight |
| *Polyunsaturated fatty acids (DHA, DPA) | 100-600 |

Example 6

| Composition For Protecting Against Periodontal Inflammatory Disease | |
|---|---|
| Mouthwash: | |
| *Chondroitin sulfate | 0.4 M |
| *Quercetin | 0.4 M |

*In a standard mouthwash vehicle

Example 7

| Composition For Protecting Against Periodontal Inflammatory Disease Toothpaste Composition | |
|---|---|
| Toothpaste, | mg %: |
| *Chondroitin sulfate | 5 |
| *Quercetin | 3 |
| *D-glucosamine sulfate | 5 |
| *Olive kernel extract | 1 |

*In a standard toothpaste vehicle

Example 8

| Composition For Protecting Against the Inflammation of Sunburn | |
|---|---|
| Ingredients | % by weight |
| *Chondroitin sulfate | 5 |
| *D-glucosamine sulfate | 5 |
| *Quercetin | 3 |
| *Aloe vera | 10 |
| *Olive kernel extract | 5 |
| *Sun screen (e.g., $TiO_2$) | 5 |

Example 9

| Oral Composition For Protecting Against Migraine Headaches | |
|---|---|
| Ingredients | mg: |
| *Chondroitin sulfate | 50 |
| *Quercetin | 100 |
| *Azatadine | 4 |
| *Optionally, a CRH-receptor antagonist | 5-300 |

Example 10A

| Oral Composition For Protecting Against Inflammation in Relapsing Multiple Sclerosis | |
|---|---|
| Ingredients, | mg/day |
| *Quercetin | 50-300 |
| *Chondroitin sulfate | 50-300 |
| *Rutin | 50-300 |
| *Hydroxyzine | 50-300 |
| *Olive kernel extract | 350-1200 |
| *Optionally, interferon-beta | 8 million IU Betaferon (Schering), s.c., on alternate days or 30 µg Avonex |
| *Optionally, glatiramer acetate | Copaxone NPR by parenteral injection |

Example 10B

| General Composition for Protecting Against the Brain Inflammation of Multiple Sclerosis | |
|---|---|
| Components | Mg/tablet or capsule |
| Quercetin | 100-1000 |
| Rutin | 100-1000 |
| (−)Epigallocatechin-gallate | 100-1000 |
| Docosohexanoic acid (DHA) | 100-1000 |
| Krill oil | 100-1000 |
| Olive kernel extract | 100-1000 |

Example 10C

| Specific Composition for Protecting Against Multiple Sclerosis | |
|---|---|
| Components | Amounts |
| Quercetin, rutin, (−)epigallocatechin3-gallate, Docosohexanoic acid | Each 150 mg/tab or cap. |
| Krill oil | 50 mg |
| Olive kernel extract | 450 mg |

Example 11

| Composition For Protecting Against the Inflammation of Cystitis And Prostatitis | |
|---|---|
| Ingredients, | mg/capsule or tablet: |
| *D-Glucosamine sulfate | 50 |
| *Chondroitin sulfate | 100-300 |
| *Sodium hyaluronate | 200 |
| *Quercetin | 100-400 |
| *Olive kernel extract | 350-1200 |

Example 12

| Composition For Protecting Against Inflammatory "Flush" | |
|---|---|
| Ingredients, | per capsule: |
| *Chondroitin sulfate | 50 mg |
| *Quercetin | 150-350 mg |
| *Olive kernel extract | 100-750 mg |
| *Bitter willow bark extract | 5% by weight |
| *Optionally, cyproheptadine or azatadine | 4 mg |

Example 13

| Cream Composition For Protecting Against Inflammatory Skin Allergy | |
|---|---|
| Ingredients: | % by weight |
| *Aloe vera | 5 |
| *Non-bovine chondroitin sulfate | 5 |
| *Myricetin | 5 |
| *Alpha-tocopherol | 5 |
| *Olive kernel extract | 5 |
| *Aloe vera | 10 |
| *Optionally, azelastine or hydroxyzine | 5 |

Example 14

| Composition For Protecting Against Inflammatory Allergies and Allergic Asthma | |
|---|---|
| Ingredients, | mg/tablet |
| *Myricetin | 500 |
| *Chondroitin sulfate | 200 |
| *Optionally, azelastine | 4 |
| *Rutin | 500 |
| *Optionally, hydroxyzine | 25 |

Example 15

| Composition For Protecting Against Brain Metastases from Breast Cancers | |
|---|---|
| Ingredients, | mg/day |
| Chondroitin sulfate | 50-300 |
| Quercetin | 25-250 |
| Genestein | 50-300 |
| Phenoxodiol isoflavone | 500-1000 |
| Olive kernel extract | 350-1200 |
| Optionally, tomoxifen or raloxifen | About 10 |

Example 16

| Composition For Protecting Against the Inflammation of Allergic Conjunctivitis | |
|---|---|
| Ingredients: | Weight % |
| *Quercetin | 0.05% |
| *Chondroitin sulfate | 2.0% |
| *Optionally, azelastine | 0.05% |

Example 17

Effect of Olive Kernel Extract on Absorption of a Proteoglycan Sulfate In Vivo

Chondroitin sulfate was tritiated by New England Nuclear Corp. to a specific activity of 4.3 mCi/ml.

Unlabeled chondroitin sulfate was dissolved in olive kernel extract at a ratio of about 55 w/v chondroitin sulfate powder to about 450 w/v of olive kernel extract (2.9% acidity as oleic acid, 1.03% water, 0.08% hexane). To this solution was added 20.2 microcuries of the labeled chondroitin sulfate. AAA gelatin capsules were filled with the resulting solution using an aluminum template molding device.

The laboratory animals (250 g male Sprague-Dawley rats) were kept overnight without food but with free access to water. One capsule containing the above-described chondroitin sulfate-olive kernel extract solution was given to each rat per os. Control animals were given the equivalent amount of chondroitin, but without olive kernel extract. The animals were then given free access to food. Serum radioactivity was measured 8 hours thereafter in a beta scintillation counter.

The results showed that, in control animals, about 3.9%+/−0.4% (n=3) of the dose of labeled chondroitin sulfate reached the circulation. In sharp contrast, in animals given the olive kernel extract along with the labeled chondroitin sulfate, about 14.3%+/−0.7% (n=4) of the dose was absorbed into the general circulation.

These results demonstrate that olive kernel extract increased by almost 400% the absorption of a proteoglycan from the intestine into the general circulation.

Parallel experiments with codfish oil, corn oil and olive oil (from the flesh of the olive) were contemplated, but chondroitin sulfate solubility in these oils was insufficient to meet the requirements of the experiment.

Example 18

| Composition for Protecting Against Inflammatory Endometriosis | |
| --- | --- |
| Ingredients | mg/tablet |
| *Rutin | 300 |
| *Quercetin | 300 |
| *Olive kernel extract | 300 |

The invention claimed is:

1. A method of treating neurodegenerative brain inflammation in a subject, comprising administering to a subject in need thereof an effective amount of a composition comprising a flavonoid or a flavonoid glycoside, olive kernel oil, a proteoglycan and one or more ingredients selected from the group consisting of a polyunsaturated fatty acid and a phospholipid.

2. The method of claim 1, wherein the composition further comprises an interferon.

3. The method of claim 1, wherein the composition further comprises glutiramer acetate.

4. The method of claim 1, wherein the composition further comprises a histamine-1 receptor antagonist.

5. The method of claim 1, wherein the flavonoid is selected from the group consisting of quercetin, myricetin, genistein, kaempferol, (−)epigallocatechin-3-gallate, luteolin, epigenin, rutin, hesperitin, and hesperidin.

6. The method of claim 1, wherein the composition comprises a polyunsaturated fatty acid, and wherein the polyunsaturated fatty acid is selected from the group consisting of alphalinoleic acid, eicosapentenoic acid, and docosahexenoic acid.

7. The method of claim 1, wherein the composition comprises a phospholipid, and wherein the phospholipid is selected from the group consisting of fish oil, Krill oil, and sphingomyelin.

8. The method of claim 1, wherein the composition comprises chondroitin sulfate, a flavonoid, docosahexenoic acid, Krill oil, and olive kernel oil.

9. The method of claim 8, wherein the composition further comprises hydroxyzine.

10. The method of claim 8, wherein the composition is administered orally.

11. The method of claim 1, wherein each ingredient is in the amount of 100-1,000 mg.

12. The method of claim 1, wherein the composition comprises chondroitin sulfate, quercetin, rutin, (−)epigallocatechin-3-gallate, docosahexenoic acid, and olive kernel oil.

13. The method of claim 12, wherein the composition comprises 150 mg of quercetin, 150 mg of rutin, 150 mg of (−)epigallocatechin-3-gallate, 250 mg of docosahexenoic acid, 300 mg of olive kernel oil and chondroitin sulfate.

14. The method of claim 12, wherein the composition further comprises hydroxyzine.

15. The method of claim 12, wherein the composition is administered orally.

16. The method of claim 1, wherein the neurodegenerative brain inflammation includes disruption of the blood-brain barrier.

17. A composition comprising 10-1000 mg of luteolin, 10-1000 mg of quercetin, 10-1000 mg of rutin, 100-1000 mg of (−)epigallocatechin-3-gallate, 100-1000 mg of docosahexenoic acid, 100-1000 mg of krill oil, and 100-1000 mg of olive kernel oil.

18. The composition of claim 17, wherein the composition further comprises 10-1000 mg of chondroitin sulfate.

19. The composition of claim 18, wherein the composition comprises 150 mg of luteloin, 150 mg of quercetin, 150 mg of rutin, 150 mg of (−)epigallocatechin-3-gallate, 250 mg of docosahexenoic acid, 300 mg of olive kernel oil and 10-1000 mg of chondroitin sulfate.

* * * * *